US 6,660,011 B2

(12) United States Patent
Levinson

(10) Patent No.: US 6,660,011 B2
(45) Date of Patent: Dec. 9, 2003

(54) TISSUE CUTTING AND RETRIEVAL DEVICE AND METHOD

(76) Inventor: Melvin E. Levinson, 12700 SW. 64 Ct., Pinecrest, FL (US) 33156

( * ) Notice: Subject to any disclaimer, the term of this patent is extended or adjusted under 35 U.S.C. 154(b) by 0 days.

(21) Appl. No.: 10/245,116

(22) Filed: Sep. 17, 2002

(65) Prior Publication Data

US 2003/0176859 A1 Sep. 18, 2003

Related U.S. Application Data

(63) Continuation-in-part of application No. 10/057,422, filed on Jan. 24, 2002, now Pat. No. 6,585,734.
(60) Provisional application No. 60/322,763, filed on Sep. 17, 2001.

(51) Int. Cl.[7] ............................................... A61B 17/24
(52) U.S. Cl. ......................................... 606/113; 606/47
(58) Field of Search .............................. 606/41, 47, 113, 606/127, 128

(56) References Cited

U.S. PATENT DOCUMENTS

| 4,503,855 | A | | 3/1985 | Maslanka |
| 5,397,320 | A | | 3/1995 | Essig et al. |
| 5,997,536 | A | | 12/1999 | Osswald et al. |
| 6,013,086 | A | * | 1/2000 | Ouchi et al. ................. 606/113 |
| 6,099,534 | A | * | 8/2000 | Bates et al. ................. 606/127 |
| 6,152,922 | A | * | 11/2000 | Ouchi ........................... 606/47 |
| 6,306,133 | B1 | * | 10/2001 | Tu et al. ........................ 606/41 |

* cited by examiner

*Primary Examiner*—Michael Peffley
(74) *Attorney, Agent, or Firm*—McDermott, Will & Emery

(57) ABSTRACT

A device for cutting and retrieving tissue, including a handle having a tube, a first set of wires positioned within the tube and extending from the handle to distal ends, and a control tip at the distal ends thereof. A second set of wires are positioned within the tube and extend from the handle. A retaining pin portion at the control tip, extends between at least two of the second set of wires, allows the second set of wires to be extended from the tube and through the control tip, and prevents the second set of wires from being withdrawn from the control tip and into the tube. The retaining pin portion also extends the second set of wires from the tube upon the first set of wires being extended from the tube.

20 Claims, 4 Drawing Sheets

TISSUE CUTTING AND RETRIEVAL DEVICE AND METHOD

CROSS-REFERENCE TO RELATED APPLICATIONS

This application is a continuation in part of U.S. patent application Ser. No. 10/057,422, filed on Jan. 24, 2002, now U.S. Pat. No. 6,585,734, the disclosure of which is incorporated herein by reference. U.S. patent application Ser. No. 10/057,422 claims priority to provisional U.S. patent application Ser. No. 60/322,763, filed on Sep. 17, 2001.

FIELD OF THE INVENTION

This invention generally relates to a surgical instrument assembly for use in cutting and retrieving objects from internal body cavities and, more specifically, to a surgical instrument assembly for use in snare cauterization procedures. The present invention also relates to a method for cutting and retrieving objects from internal body cavities and, in a preferred form, to a method for cutting, capturing and/or retrieving polyps and other aggregates of organic tissue from a patient's internal organs via a snare cauterization procedure.

BACKGROUND OF THE INVENTION

A wire snare has been used in many different configurations and for many different medical uses. The snare, when equipped for use with cautery, has been used for polypectomies. For example, during a colonoscopy, or other endoscopic procedures, a wire loop or snare, combined with cautery, is frequently used to biopsy or excise lesions. While a wire loop or snare is very effective at cutting free a lesion, it has substantially no ability to capture and/or retrieve the excised lesion.

Typically, a second instrument is used to retrieve the excised lesion. The second instrument most often is provided in the form of a wire basket having several loops angularly offset and preferably, but not necessarily, perpendicular to each other in the case of two loops and designed to trap the excised lesion, such as a stone basket used in urology and gastroenterology. The use of two different instruments, one instrument to cut and a second instrument to retrieve, however, is inconvenient, inefficient, time consuming and can sometimes lead to the loss of the excised lesion.

What is still desired is a single instrument that can snare and retrieve a lesion. Preferably, the instrument will be simple in design and reliable in use, and will allow repeated use of a snare or a retrieval configuration, as required, by simple mechanical means.

SUMMARY OF THE INVENTION

The present invention provides a simple, but elegant solution to this problem by providing a device for selectively capturing, cutting and retrieving tissue, wherein the device includes a cutting snare, or cauterization wires, that can be incorporated into a retrieval basket configuration also including a basket snare, or basket wires, without removing the cutting snare from a patient's body. It also allows repeated use of the basket or the snare configuration, as required, by simple mechanical means.

According to one aspect of the present invention, the device includes a handle having an elongated, flexible tube extending therefrom along a central axis to a distal end, a first set of elongated, flexible wires slidingly positioned within the tube and extending along the central axis from the handle to distal ends for extending out of the distal end of the tube, a control tip secured to the distal ends of the first set of wires, the control tip having a slot, and a second set of elongated, flexible wires slidingly positioned within the tube and extending along the central axis from the handle, through the slot in the control tip, to distal ends, the second set of wires being coupled at the distal ends. A retaining pin is secured to the control tip and extends transversely through the slot of the control tip and between the second set of wires. The retaining pin allows the coupled distal ends of the second set of wires to be extended from the control tip, and prevents the coupled distal ends of the second set of wires from being withdrawn from the slot of the control tip and into the tube. In addition, the retaining pin drives the coupled distal ends of the second set of wires from the distal end of the tube upon the distal ends of the first set of wires being driven from the distal end of the tube.

According to one aspect of the present invention, the first and second sets of wires have a preset shape, preferably curving in an arc near their distal ends, so that when within the tube, the wires are substantially coaxial with the tube, but when extended from the tube, their distal ends form a loop.

According to an additional aspect of the present invention, the control tip is a discrete element that is secured to the first set of wires and the slot of the control tip is oriented such that a first reference plane formed by the loops of at least two of the wires of the first set and a second reference plane formed by the loops of at least two of the wires of the second set are angularly offset. According to a further aspect, the first reference plane is substantially perpendicular to the second reference plane.

According to still another aspect of the present invention, the first set of wires includes only two wires. According to an additional aspect, the second set of wires includes only two wires.

According to a further aspect of the present invention, the device includes a first deployment assembly operatively connected to the first set of wires and allowing a user to selectively extend and withdraw the distal ends of the first set of wires from the distal end of the tube, and a second deployment assembly operatively connected to the second set of wires and allowing a user to selectively extend and withdraw the distal ends of the second set of wires from the distal end of the tube. According to another aspect, a latching mechanism is provided for connecting the first and second deployment assemblies. In accordance with an additional aspect, a locking mechanism is provided for preventing movement of the first deployment assembly.

According to another aspect of the present invention, the first set of wires of the device is formed by a single continuing wire folded at a distal end, instead of two wires connected to a discrete control tip. The distal end of the continuing retrieving wire forms a "control tip", preferably an "S" or "8-like" shape structure having two apertures and one effective retaining pin portion in the middle. Two wires of the second set of wires (cutting wires) are joined at a distal end and are slidingly positioned within the tube, extending along the central axis from the handle, and wherein each wire of the set passes through one of the two apertures of the control tip. The distal end of the cutting wires is retained by the retaining pin. The "S" or "8-like" shape control tip replaces the discrete control tip of the previously described embodiment, functioning as a retaining pin for retaining the cutting wires, and also as a bottom of a "basket" formed by the retrieving wires and the cutting wires, used to retrieve tissue.

The present invention also provides a method for selectively capturing, cutting and retrieving tissue in a body cavity using a device as defined above. The method includes inserting into the body cavity the distal end of the elongated, flexible tube, and manipulating the second set of wires from the handle so that distal ends of the second set extend from the distal end of the tube and capture tissue to be cut between at least two wires of the second set. A cauterizing current is then applied to the second set of wires such that the tissue is cut, and the first set of wires is manipulated from the handle so that the distal ends of the first set of wires and the control tip extend from the distal end of the tube and capture the cut tissue between the first and the second sets of wires. The distal end of the tube, together with the first and the second sets of wires and the cut and captured tissue, is subsequently withdrawn from the body cavity.

A monopolar RF electrocautery is used in one preferred embodiment. RF energy is applied to the cutting wires at proximal ends of the cutting wires from an external source. Ground conductor is appropriately positioned external to the patient.

These and other features and benefits of the presently disclosed device and method will become more apparent upon reading the following specification in combination with the accompanying drawing figures.

BRIEF DESCRIPTION OF THE DRAWINGS

Like reference characters designate identical or corresponding components and units throughout the several views.

DETAILED DESCRIPTION OF AN EXEMPLARY EMBODIMENT

Figure 1:
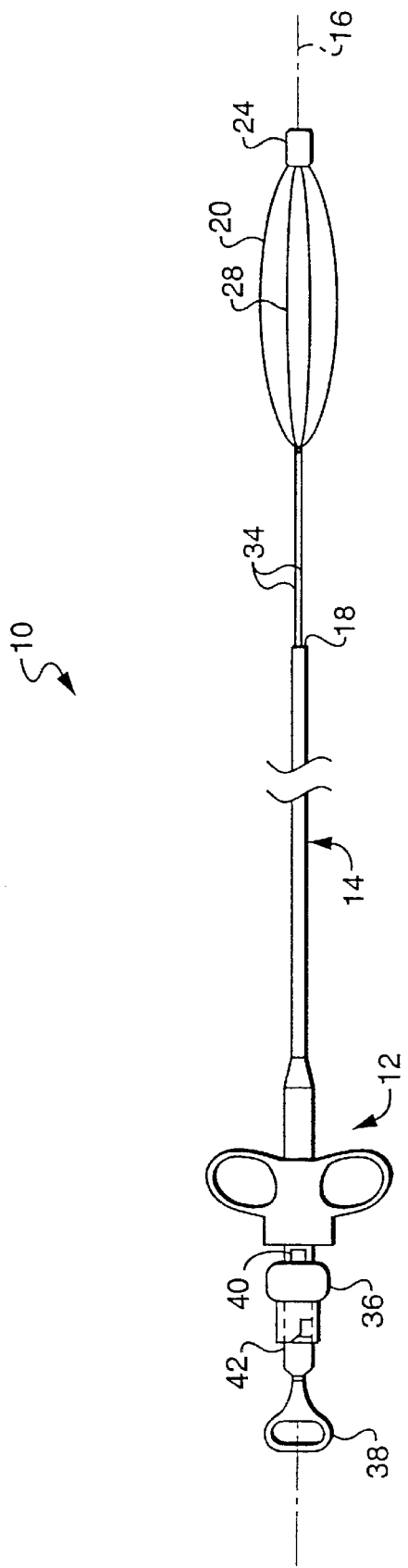
FIG. 1 is a side elevation view of an exemplary embodiment of a device constructed in accordance with the present invention for selectively capturing, cutting and retrieving tissue.

Referring first to FIG. 1, there is shown an exemplary embodiment of a device 10 constructed in accordance with the present invention for selectively capturing, cutting and retrieving tissue from within an interior cavity of a patient. The device 10 generally includes a handle 12 having an elongated, flexible tube 14 extending therefrom along a central axis 16 to a distal end 18.

Figure 2:
FIG. 2 is a top plan view of a first set of (or "basket") wires and a control tip of the device of FIG. 1.
Figure 3:
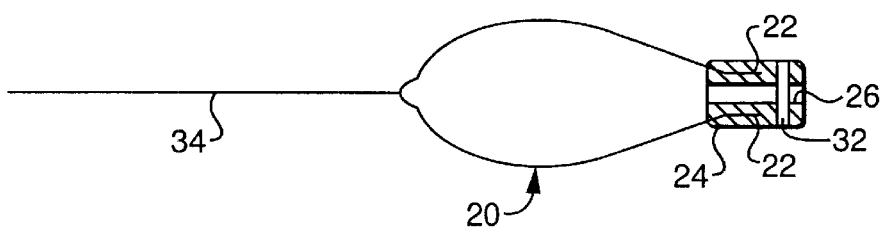
FIG. 3 is a side elevation view, partially in section, of the first set of wires and the control tip of the device of FIG. 1.
Figure 4:
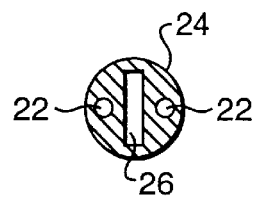
FIG. 4 is a sectional view of the first set of wires and the control tip of the device of FIG. 1, taken along line 4—4 of FIG. 2.
Figure 5:
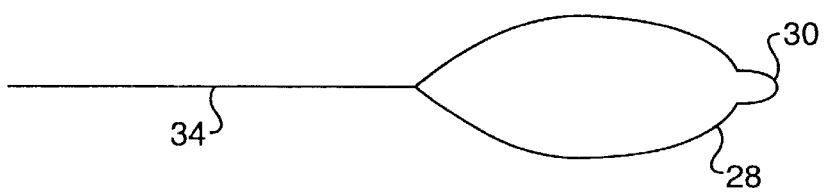
FIG. 5 is a side elevation view of a second set of (or "cauterization") wires of the device of FIG. 1.
Figure 6:
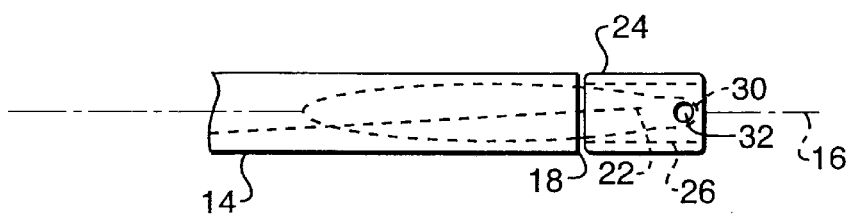
FIG. 6 is an enlarged side elevation view of the first set of wires extending out of a tube of the device of FIG. 1, the control tip positioned adjacent a distal end of the tube, and the second set of wires extending out of the tube and through the control tip.

A first set of elongated, flexible wires 20 is slidingly positioned within the tube 14 and extends along the central axis 16 from the handle 12 to distal ends 22 extending out of the distal end 18 of the tube 14. The first set of wires 20 is also shown in FIGS. 2, 3 and 6. A control tip 24 is secured to the distal ends 22 of the first set of wires 20, as also shown in FIGS. 2, 3, 4 and 6. A second set of elongated, flexible wires 28 is slidingly positioned within the tube 14 and extends along the central axis 16 from the handle 12, through a slot 26 in the control tip 24, to distal ends. The slot 26 of the control tip 24 is shown best in FIGS. 3, 4 and 6. The second set of wires 28 is coupled at the distal ends 30, as shown in FIGS. 5 and 6.

A retaining pin 32 is secured to the control tip 24 and extends through the slot 26 of the control tip 24 and between at least two wires of the second set of wires 28. The retaining pin 32, which is shown best in FIGS. 2, 3 and 6, allows the distal ends 30 of the second set of wires 28 to be extended through the control tip 24, and prevents the coupled distal ends 30 of the second set of wires 28 from being withdrawn from the slot 26 of the control tip 24 and into the tube 14. In addition, the retaining pin 32 extends the distal ends 30 of the second set of wires 28 from the distal end 18 of the tube 14 upon the distal ends 22 of the first set of wires 20 being extended from the distal end of the tube 14.

In the exemplary embodiment shown in the drawings, the first set of wires 20 includes two wires, and the second set of wires 28 includes two wires. It should be understood, however, that the first and second sets of wires 20, 28 can each be provided with more than two wires. The wires are formed of a thin spring or shape metal which allows the wires to completely collapse and be retracted into the tube 14 and expand upon being extended from the distal end 18 of the tube 14. Preferably, each of the first and the second sets of wires 20, 28 are formed such that they each expand to an oval loop upon being extended from the distal end of the tube 14, but can be formed to expand to other shapes, such as a spiral shape. The first and the second sets of wires 20, 28 are formed from shape-memory metals such as stainless steel and nitinol, which have "memory" or the ability to retain their original shape when extended from the tube 14. The sets of wires 20, 28 can utilize hollow or solid extensions 34 from the handle 12, and can either pass side by side through the tube 14, or one extension can extend through the other extension (such as hypotube) for more accurate approximation.

The control tip 24 is secured to the first set of wires 20 and the slot 26 of the control tip 24 is oriented such that a first reference plane formed by at least two of the wires of the first set 20 and a second reference plane formed by at least two of the wires of the second set 28 are angularly offset. Preferably, the control tip 24 holds the two sets of wires 20, 28 such that the first reference plane is substantially perpendicular to the second reference plane, so that the wires form a desired "retrieval basket" when both sets of wires 20, 28 are extended as shown in FIG. 1. The tube 12, the control tip 24 and the pin 32 can each be made of stainless steel or Teflon® or other suitable material.

Referring to FIG. 1, the handle 12 of the device 10 includes a first deployment assembly 36 operatively connected to the first set of wires 20 and allowing a user to selectively extend and withdraw the distal ends 22 of the first set of wires 20 from the distal end 18 of the tube 14, and a second deployment assembly 38 operatively connected to the second set of wires 28 and allowing a user to selectively extend and withdraw the distal ends 30 of the second set of wires 28 from the distal end 18 of the tube 14. The handle 12 also includes a latching mechanism 40 that allows a user to latch the first and second deployment assemblies 36, 38, such that movement of one assembly causes movement of both assemblies, e.g., when the device 10 is being used as a retrieval tool. In addition, the handle 12 is provided with a locking mechanism 42 that allows a user to prevent movement of the first deployment assembly 36 during operation of the second deployment assembly 38, e.g., when the device 10 is being used as a cutting tool. In this manner, the device 10 can be simply configured for cutting and retrieval without removing the device 10 from an internal body cavity of patient. Although not shown, the device 10 includes a connector for connecting the second set of wires 28 to a source of power, e.g., cauterizing current, for energizing the second set of wires 28 so that the wires cut tissue captured within the second set of wires 28.

Figure 8B:
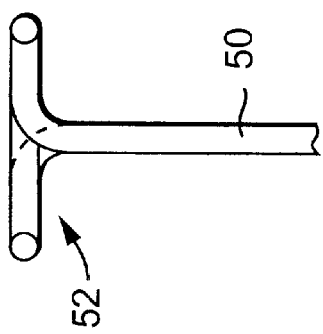
FIG. 8B is a side elevation view of the first set of wires of the embodiment of FIG. 7.
Figure 8A:
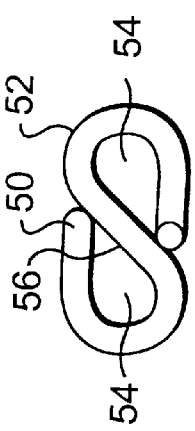
FIG. 8A is a top plan view of the first set of wires of the embodiment of FIG. 7.
Figure 7:
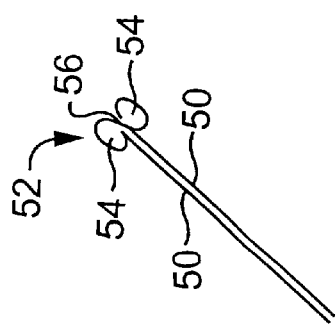
FIG. 7 is a perspective view of a first set of wires of the present invention.

In another preferred embodiment of the present invention, as shown in FIG. 7, FIG. 8A and FIG. 8B, the first set of wires of the device 10 is formed by a single continuing retrieving wire 50 instead of two wires 20 joined at their distal ends by a discrete cap tip. The retrieving wire 50 has a distal end 52, which forms a control tip, preferably an "S" or "8-like" shape structure having two apertures 54 and one portion 56 effectively forming a retaining pin in the middle. The wires of the second set of wires 28 (cutting wires) are joined at their distal ends, and are slidingly positioned within the tube 14, extending along the central axis from the handle 12. Each wire of the second set passes through the one of the two apertures 54 of the control tip. The distal end 30 of the cutting wires 28 is retained by the retaining pin 56. The "S" or "8-like" shaped control tip 52 replaces the control tip 24 of the previously described embodiment, functioning as a retaining pin for retaining cutting wires 28, and also as a bottom of retrieving wire 50 to retrieve tissues.

Figure 9:
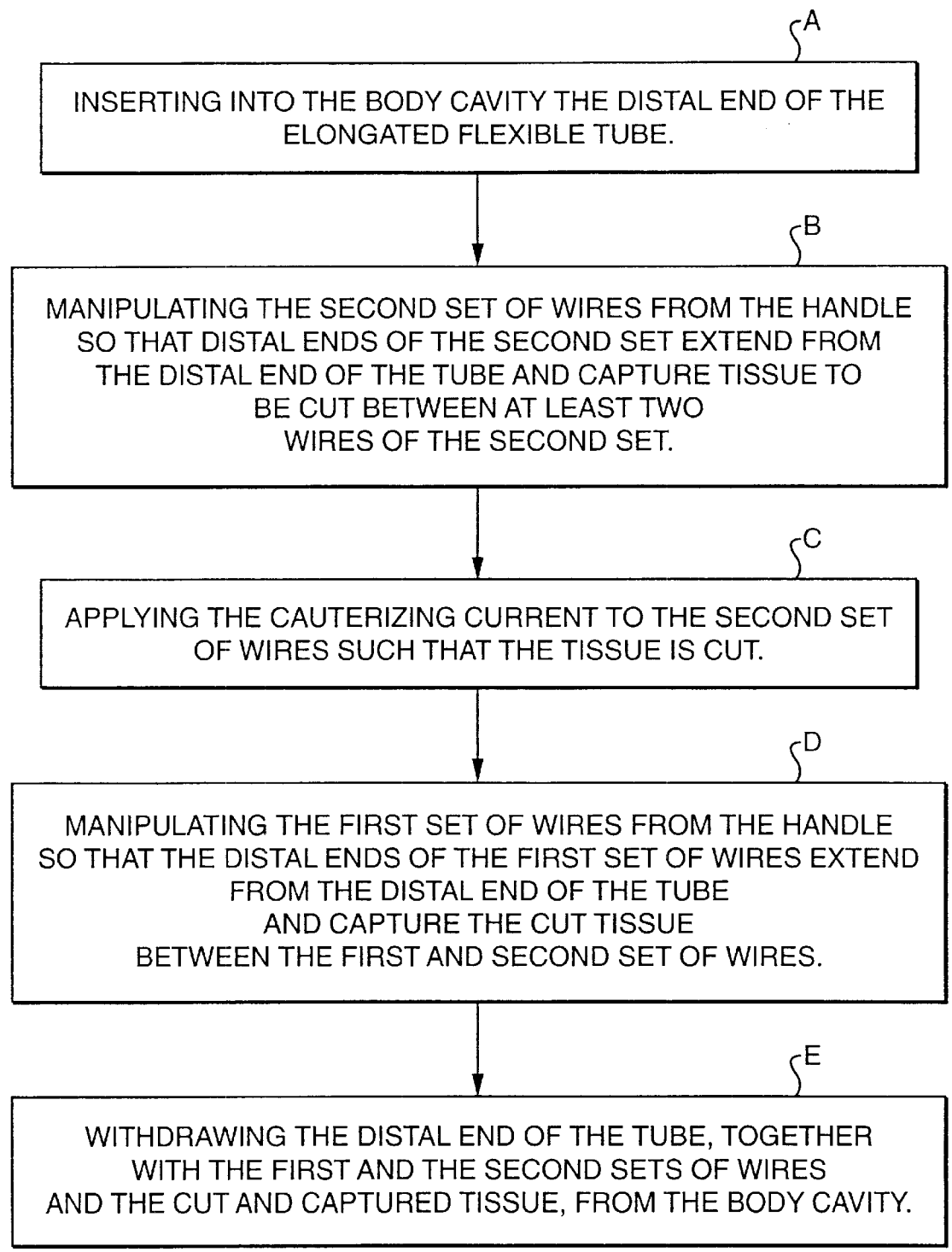
FIG. 9 is a flow chart illustrating a method according to the present invention for selectively capturing, cutting and retrieving tissue.

Referring to FIG. 9, the present invention also provides a method for selectively capturing, cutting and retrieving tissue in a body cavity using the device 10 of FIGS. 1 through 8. The method includes inserting into the body cavity the distal end of the elongated, flexible tube, as shown at "A", and manipulating the second set of wires from the handle assembly so that distal ends of the second set of wires extend from the distal end of the tube and capture tissue to be cut between at least two wires of the second set, as shown at "B". A cauterizing current is then applied to the second set of wires such that the tissue is cut, as shown at "C", and the first set of wires, and the control tip of the first set of wires are manipulated from the handle assembly so that the distal ends of the first set of wires extends from the distal end of the tube and capture the cut tissue between the first and the second sets of wires, as shown at "D". The distal end of the tube, together with the first and the second sets of wires and the cut and captured tissue, is subsequently withdrawn from the body cavity, as shown at "E".

A monopolar RF electrocautery is used in one preferred embodiment. RF energy is applied to the cutting wires at proximal ends of the cutting wires from an external source. Ground conductor is appropriately positioned external to the patient.

The present invention, accordingly, provides a device and a method which allows a single instrument to function as a tissue cutting snare and a basket retriever. By replacing two or more existing instruments with a simply manufactured and easily utilized device, the present invention beneficially provides a useful, new and improved device and method for endoscopically cutting and retrieving tissue.

Modifications to the above-described exemplary embodiment of the presently disclosed invention may become apparent to those skilled in the art. The scope of the invention is therefore intended to be limited solely by the scope of the appended claims.

What is claimed is:

1. A device for selectively capturing, cutting and retrieving tissue, comprising:
   A) a handle having an elongated, flexible tube extending therefrom along a central axis to a distal end;
   B) a first set of elongated, flexible wires slidingly positioned within the tube and extending along the central axis from the handle to joined distal ends for extending out of the distal end of the tube;
   C) a second set of elongated, flexible wires slidingly positioned within the tube and extending along the central axis from the handle to joined distal ends for extending out of the distal end of the tube; and
   D) a control tip joining the distal ends of the first set of wires and including a transverse portion extending beyond the distal end of the tube in a direction transverse to the central axis, the transverse portion being adapted for interfering engagement with the distal end of said tube, thereby preventing the distal ends of said first set of wires from being wholly drawn into said tube, and
   wherein the wires of said first set and said control tip are formed from a single wire, said control tip having a substantially S shape defining two apertures separated by a retaining pin portion, and wherein the wires of said second set pass on opposite sides of said retaining pin portion and through an associated one of said apertures; and
   wherein said retaining pin portion is adapted for interfering engagement of the joined distal ends of said second set of wires, thereby maintaining said distal ends of said second set of wires farther from said distal end of said tube than said control tip.

2. A device according to claim 1, wherein the first set of wires includes two wires.

3. A device according to claim 1, wherein at least two of the wires of the first set define a first reference plane and at least two of the wires of the second set define a second reference plane, and wherein the first reference plane and the second reference plane are angularly offset.

4. A device according to claim 3, wherein the first reference plane is substantially perpendicular to the second reference plane.

5. A device according to claim 1, wherein the wires have shape memory such that each of the first and the second sets of wires expand upon being extended from the distal end of the tube.

6. A device according to claim 5, wherein each of the first and the second sets of wires expand to an oval loop upon being extended from the distal end of the tube.

7. A device according to claim 1, further comprising:
   F) a first deployment assembly operatively connected to the first set of wires and allowing a user to selectively extend and withdraw the distal ends of the first set of wires from the distal end of the tube; and
   G) a second deployment assembly operatively connected to the second set of wires and allowing a user to selectively extend and withdraw the distal ends of the second set of wires from the distal end of the tube.

8. A device according to claim 7 further comprising a latching mechanism for connecting the first and second deployment assemblies.

9. A device according to claim 7 further comprising a locking mechanism for preventing movement of the first deployment assembly.

10. A device for selectively capturing, cutting and retrieving tissue, comprising:
   A) a handle having an elongated, flexible tube extending therefrom along a central axis to a distal end;
   B) a first set of elongated, flexible wires slidingly positioned within the tube and extending along the central axis from the handle to distal ends for extending out of the distal end of the tube;
   C) a control tip disposed at the distal ends of the first set of wires, and wherein the wires of said first set and said control tip are formed from a single wire, said control tip having a substantially S shape defining two apertures separated by a retaining pin portion;
   D) a second set of elongated, flexible wires slidingly positioned within the tube and extending along the central axis from the handle, said second set of wires passing on opposite sides of said retaining pin portion of said control tip and through an associated one of the apertures in the control tip, to distal ends, the second set of wires coupled at the distal ends; and
   E) wherein the retaining pin portion allows the distal ends of the second set of wires to be extended through the control tip, and preventing the coupled distal ends of the second set of wires from being withdrawn from the apertures of the control tip and into the tube, the retaining pin portion extending the distal ends of the second set of wires from the distal end of the tube upon the distal ends of the first set of wires being extended from the distal end of the tube.

11. A device according to claim 10, wherein the second set of wires includes two wires.

12. A device according to claim 10, wherein a first reference plane defined by at least two of the wires of the first set and a second reference plane defined by at least two of the wires of the second set are angularly offset.

13. A device according to claim 12, wherein the first reference plane is substantially perpendicular to the second reference plane.

14. A device according to claim 10, wherein the wires have shape memory such that each of the first and the second sets of wires expand upon being extended from the distal end of the tube.

15. A device according to claim 14, wherein each of the first and the second sets of wires expand to an oval loop upon being extended from the distal end of the tube.

16. A device according to claim 10, further comprising:
   F) a first deployment assembly operatively connected to the first set of wires and allowing a user to selectively extend and withdraw the distal ends of the first set of wires from the distal end of the tube; and
   G) a second deployment assembly operatively connected to the second set of wires and allowing a user to selectively extend and withdraw the distal ends of the second set of wires from the distal end of the tube.

17. A device according to claim 16 further comprising a latching mechanism for connecting the first and second deployment assemblies.

18. A device according to claim 16 further comprising a locking mechanism for preventing movement of the first deployment assembly.

19. A device for selectively capturing, cutting and retrieving tissue, comprising:
   A) a handle having an elongated, flexible tube extending therefrom along a central axis to a distal end, said tube having a diameter D at its distal end;
   B) a first pair of elongated, flexible wires slidingly positioned within the tube and extending along the central axis from the handle to continuously joined distal ends for extending out of the distal end of the tube, wherein said joined distal ends include a control tip wire portion extending a distance larger than D in a direction transverse to said central axis, said control tip wire portion defining two apertures separated by a retaining portion, wherein the first pair of wires and said control tip portion are formed from a single wire,
   C) a second pair of elongated, flexible wires slidingly positioned within the tube and extending along the central axis from the handle, to joined distal ends, wherein each wire of said second pair passes on opposite sides of said retaining portion and through an associated one of said apertures of said control tip wire portion,
      wherein said distal ends of said first pair of wires and said second pair of wires are each adapted for selective positioning along said central axis between points adjacent to said distal end of said tube and points distal therefrom.

20. A device according to claim 19, wherein said selective positioning of said first pair of wires and said selective positioning of said second pair of wires are independently controllable, with said distal ends of said second pair of wires being farther from said distal end of said tube than said distal ends of said first pair of wires.

* * * * *